(12) United States Patent
Hall

(10) Patent No.: US 7,473,816 B2
(45) Date of Patent: Jan. 6, 2009

(54) MULTILAYER MOISTURE MANAGEMENT FABRIC

(75) Inventor: Michael R. Hall, Topeka, KS (US)

(73) Assignee: Lohmann & Rauscher, Inc., Topeka, KS (US)

( * ) Notice: Subject to any disclaimer, the term of this patent is extended or adjusted under 35 U.S.C. 154(b) by 578 days.

(21) Appl. No.: 10/848,256

(22) Filed: May 18, 2004

(65) Prior Publication Data

US 2005/0261617 A1 Nov. 24, 2005

(51) Int. Cl.
*A61F 5/00* (2006.01)
(52) U.S. Cl. .............................. 602/41; 602/42; 602/46
(58) Field of Classification Search ............. 602/41–47, 602/52–54, 56
See application file for complete search history.

(56) References Cited

U.S. PATENT DOCUMENTS

| | | | |
|---|---|---|---|
| 2,238,878 A | 4/1941 | Baitz et al. | |
| 2,310,082 A | 2/1943 | Holbrooke | |
| 2,592,801 A | 4/1952 | Hanington | |
| 2,787,266 A | 4/1957 | Scholl | |
| 2,811,154 A | 10/1957 | Scholl | |
| 3,457,919 A | 7/1969 | Harbard | |
| 3,880,155 A | 4/1975 | Rosoff | |
| 3,983,870 A | 10/1976 | Herbert et al. | |
| 4,445,505 A | 5/1984 | Labour et al. | |
| 4,495,661 A * | 1/1985 | Kamat | ............... 2/97 |
| 4,699,133 A | 10/1987 | Schafer et al. | |
| 4,793,337 A * | 12/1988 | Freeman et al. | ............... 602/56 |
| 4,832,010 A | 5/1989 | Lerman | |
| 4,838,253 A | 6/1989 | Brassington et al. | |
| 4,933,231 A * | 6/1990 | Seber | ............... 442/148 |
| 4,944,958 A | 7/1990 | Langen et al. | |
| 5,085,210 A | 2/1992 | Smith, III | |
| 5,156,589 A | 10/1992 | Lagnen et al. | |
| 5,277,954 A | 1/1994 | Carpenter et al. | |
| 5,352,216 A * | 10/1994 | Shiono et al. | ............... 604/312 |
| 5,413,553 A | 5/1995 | Downes | |
| 5,418,980 A | 5/1995 | Kelly | |
| 5,449,341 A | 9/1995 | Harris | |
| 5,497,513 A | 3/1996 | Arabeyre et al. | |
| 5,607,749 A | 3/1997 | Strumor | |
| 5,635,201 A | 6/1997 | Fabo | |
| 5,735,807 A | 4/1998 | Cropper | |
| 5,865,776 A | 2/1999 | Springs | |
| 5,916,187 A | 6/1999 | Brill | |
| 5,948,707 A * | 9/1999 | Crawley et al. | ............. 442/101 |
| 2003/0088202 A1 * | 5/2003 | Gilman | ............... 602/46 |

\* cited by examiner

*Primary Examiner*—Michael A. Brown
(74) *Attorney, Agent, or Firm*—John C. McMahon

(57) ABSTRACT

A multilayer breathable moisture management and compressive device, having a laminate material that includes a thin, hydrophillic polyurethane foam coated on both surfaces with an adhesive. A stretchable elastomeric polymer layer is bonded to each of the adhesive surfaces. The polymer layers preferably are microfibers having a greater number of filaments on a skin engaging side than on an opposite side thereof. The resulting device draws moisture from the skin whereby moisture generated by the underlying skin is absorbed into the device and is thereafter conveyed into the polyurethane foam and then into the outer polymer layer such that the moisture is permitted to evaporate from the surface of the device. The device may be used as a sleeve for providing compression especially during exercise or may be used as a wound dressing or the like, providing moisture management and/or heat retention under compression.

15 Claims, 2 Drawing Sheets

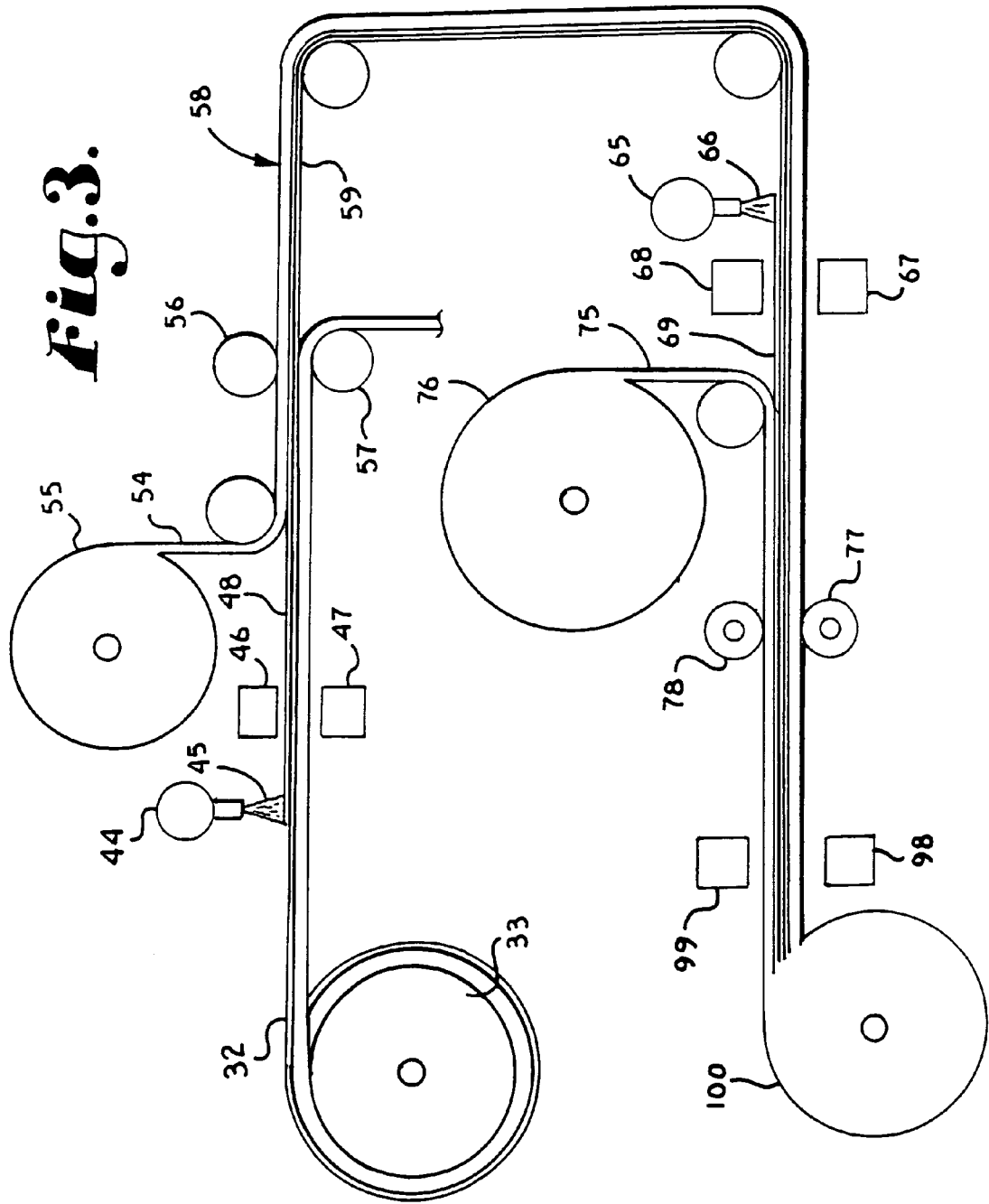

MULTILAYER MOISTURE MANAGEMENT FABRIC

BACKGROUND OF THE INVENTION

The present invention is directed to an improved breathable compressive sleeve or device constructed to convey moisture away from the skin so as to deter irritation. More particularly, it is concerned with a device of laminate multilayer construction including a hygroscopic polymeric film layer such as hydrophilic polyurethane foam for the purpose of drawing moisture from the surface of the skin and deterring the collection of moisture between the underlying skin and the device by drawing the moisture into the interior of the sleeve and toward the exterior of the device opposite the skin. The preferred sleeve construction is freely stretchable to conform to the muscles and joints of a user and provides a moisture attractant whereby moisture is pulled away from the underlying skin thus providing dry, slip-resistant compression and in certain applications support without impairing breathability of the device. The construction of the device may be utilized for compression in the form of sleeves or other compressible structures for various types of moisture management, wound care, lymphedema care and for other purposes having similar requirements.

The upright posture of the human body renders it particularly susceptible to strains, sprains and other injuries which are generally manifested by swelling, inflammation and discomfort. In addition, bed sores and the like also sometimes require compression and/or moisture management. When severe, an injury may result in impaired mobility and necessitate restriction of movement and activity or the patient may be impaired due to age or infirmity. The body is also subject to formation of fibrin clots which may obstruct vessels in the peripheral circulation when the body is in the prone position for prolonged periods. In addition to localized morbidity, such clots may also break free and travel to the heart or lungs causing more serious damage.

Orthopedic injuries have economic as well as physical repercussions for professional athletes engaged in competitive sports. Sidelined athletes lose not only the opportunity to perform, but experience a reduction in their overall level of fitness during periods of restricted activity, necessitating a period of retraining prior to resumption of competition. Of course, most individuals are not professional athletes and they engage in less strenuous activities such as jogging, calisthenics, walking and occasional competitive sports.

However, non professional athletes also experience discomfort when injured and their level of physical fitness is also impaired by injury-enforced inactivity. Moreover, amateur athletes may be more susceptible to injury, since they generally lack the advice of professional trainers as well as the fitness and judgment developed by professional athletes. Those who engage in infrequent bouts of strenuous exercise without training are most at risk of injury. However, even the well-trained amateur athlete is subject to occasional strains and sprains. Some individuals are particularly at risk of injury because of previous traumatic injury which has left continuing weakness in a joint or limb. Other individuals are at greater risk because of their advanced age or general state of health and fitness.

The importance of providing compressive support to limbs and joints which have been injured or weakened or which are subject to stress, such as may be caused by strenuous exercise, is well recognized. So-called R.I.C.E. therapy (rest, ice, compression, elevation) is commonly recommended for implementation following minor athletic injuries. Such therapy is known to be particularly effective when cold and compression are applied immediately following an injury and the compression is continued for a period of about 24 to 48 hours. The need to provide compression to facilitate venous return in bed bound patients in order to prevent formation of blood clots is similarly well recognized. It is also well known that certain wounds, wherein there are open sores or the like, respond well to compression.

Orthopedic compression bandages, braces and sleeves have long been employed to provide support for athletic and medical purposes. They are commonly worn over the wrists, elbows, knees and ankles. They are also frequently employed on the lower legs and forearms, and, less frequently, on the upper legs and arms, shoulders and chest. They provide support during normal movement, which support may be especially required by persons recovering from previous injuries or by persons who are frail or elderly. Such compression devices also provide support for ligaments, tendons, muscles and joints against the stresses of over extension which may occur during exercise. In this manner, they help to prevent orthopedic and muscular injury or reinjury or enhance wound healing or treatment. Elastomeric sleeves have also been employed, commonly in the form of stockings, to provide compression in order to facilitate peripheral venous return from the legs of bed bound patients, thereby helping to prevent embolism.

Such compression support devices are often of elastomeric construction, either in the form of sleeves, dressings or strips which may be slipped over or wound around the affected area and fastened by means of hook and loop fasteners or specialized clips or pins. Devices made in accordance with the present invention may also be used for wound care with compression or without compression where compression is not required, but where moisture management is desired, or for other purposes where moisture control next to the skin is desired.

A number of materials have been employed in the construction of such support devices. Dressing, strip and sleeve-type supports are generally constructed of knitted or woven stretchable webbing such as cotton-wound threads or synthetic resin compositions such as neoprene. Laminate multilayer composite materials have recently become available which are thinner than previously used woven material and especially neoprene. Such multilayer materials may be fabricated into sleeve or bandage-type supports and treatment devices. Multiple layer devices are often five layers thick, with a synthetic resinous film layer sandwiched between two adhesive layers, each of which is covered by an outer layer of a synthetic fabric such as nylon. In such prior art devices, the resinous film layer has been hydrophobic with respect to liquid moisture, but breathable. That is, films of this type allow passage of gas vapors, including water vapor to some extent, but generally block passage of liquid water. Therefore, because moisture produced at the skin level seldom can completely evaporate when covered, the synthetic hydrophobic resinous film layers of the prior art form an impermeable liquid moisture barrier to some degree which traps moisture against the skin within the structure.

Braces have been constructed of multiple layers. The various layers each have a purpose such as to provide protection from the cold, to provide a surface that is susceptible to cleaning or to provide a non-slip surface with a high coefficient of friction against the skin to reduce migration of the brace.

Multiple layer or single layer supports constructed of neoprene generally do not permit the underlying skin of the wearer to breathe well and trap moisture between the support and the skin. In active persons, especially athletes or persons exercising or where a wound is seeping fluid, the support or other device often beneficially traps and holds heat to aid some problems; however, the heat causes additional sweating and produces more moisture that in turn is trapped by such prior art devices against the skin. Because such impermeable supports lack the ability to carry away moisture, extended or frequent wear may be uncomfortable as well as irritating to the skin. If such irritation is prolonged, it can result in morbidity such as dermatitis and sloughing of the skin or failure of a wound to head properly. Such impermeable materials are especially unsuitable for compression bandages to be worn by amputees or individuals with impaired circulation, who may develop necroses. In addition, since impermeable supports provide no outlet for perspiration excreted by the wearer, a salt residue may be deposited on the inner surface of the support which eventually may shorten the effective life span of the support and adds to irritation of the skin.

None of the previously available materials and combinations of materials provide effective compression and/or support while providing for the removability of moisture from contact with the underlying skin surface and providing an effective system for conveying liquid moisture away from the skin. Accordingly, there is a need for various devices to convey moisture from the skin and, in particular, for a compression support sleeve for athletic and medical uses which is light weight, comfortable, stretchable to conform to the anatomy of a user and to permit moisture management and tissue movement, which enhances transport breathability of the underlying skin or circulation of the underlying blood vessels and which reduces moisture in contact with the skin by conveying moisture away from the skin to the outer surface of the support rather than trapping it between the skin and the support.

Furthermore, many worldwide national governments have determined that devices that promote retention of moisture on the surface of the skin are potentially harmful for certain uses and have passed or may soon pass legislation that favors devices for such uses that promote removal of moisture from the skin, thereby increasing the demand for devices of the type found in the present application.

SUMMARY OF THE INVENTION

The present invention resolves the problems previously outlined and provides a greatly improved compressive moisture management device which is comfortable and breathable and is especially designed to convey moisture away from underlying skin thus minimizing skin irritation. Such a device may be utilized as a breathable support sleeve to provide compression with moisture management or for other applications, including wound care.

The device preferably includes an elastomeric and freely stretchable multilayer laminate material, especially when formed into a tube, sleeve or other compression structure which is constructed to conform in shape to an intended limb or joint, such as the knee. The device is preferably tailored with gussets or darts to improve the fit and equipped with one or more support stays or pulls to facilitate placing the device on the user.

The laminate material includes a hydrophillic polymeric film, such as hydrophillic polyurethane foam, having an adhesive coating applied to either side thereof. The adhesive coatings are each in turn also bonded to respective layers of a stretchable elastomeric polymer material. The interior polymer material is preferably a polyester microfiber. By microfiber is meant a fiber in which the number of filaments in such a fiber is greater than the denier of the fiber (denier is the unit of measurement expressing the mass of a fiber divided by its length, equal to one gram per 900 meters of fiber). The preferred microfiber has relatively smaller diameter filaments (which increases the relative number of filaments for a particular fiber width) on the interior thereof facing the skin and relatively larger diameter filaments on the side of the microfiber opposite the skin. As such, the interior fiber provides a moisture attractant whereby moisture is conveyed away from the skin by the smaller diameter filament end to the larger diameter filament end and from there to the hydrophillic foam. Thereafter the outer layer helps transport moisture to the exterior at which point the moisture is increasingly subject to evaporation. For this purpose, the outer layer may also be a microfiber having smaller diameter filaments on an inward side thereof closest to the skin and larger diameter filaments on the exterior or outer surface of the device.

In certain embodiments of the invention, the compressive device may not be inherently elastic, but rather have structure that allows a person applying or adjusting the device to easily apply a desired degree of compression by snugging or pulling opposites ends of the device and then securing the opposite ends to such that the device then is compressive with respect to the user. The ends may be secured by hook and loop fasteners or other connectors that are suitable for use with the material of construction.

OBJECTS AND ADVANTAGES OF THE INVENTION

The principal objects and advantages of the present invention are: to provide a device to be utilized with a patient or user for compression, support and other uses which manages moisture and conveys moisture away from the underlying skin; to provide such a device which includes at least one layer that acts as a moisture attractant and preferably draws moisture away from the skin and to an exterior surface thereof for evaporation; to provide such a support which is cooler by nature with a higher degree of breathability than traditional supports; to provide such a device that is capable of manufacture in varying thickness and with varying degrees of elasticity to provide a desired compression at the point of application; to provide such a device which stays in place on the body of a wearer while maintaining breathability of the underlying skin; to provide such a device which is of multilayer laminate construction; to provide such a device which is light weight and comfortable to a wearer; to provide such a device which provides wind resistance; to provide such a device which provides heat retention; to provide such a device which does not irritate the skin of a wearer; to provide such a device which is comfortable to wear; and to provide a method for making a material for such a device which is simple, efficient and economical to manufacture, which effectively provides a modified wicking, breathable elastomeric surface, and which is particularly well-adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 3 is a schematic diagram illustrating a method of making a multilayer laminate material for use in construction of the compression device.

DETAILED DESCRIPTION OF THE INVENTION

Figure 1:
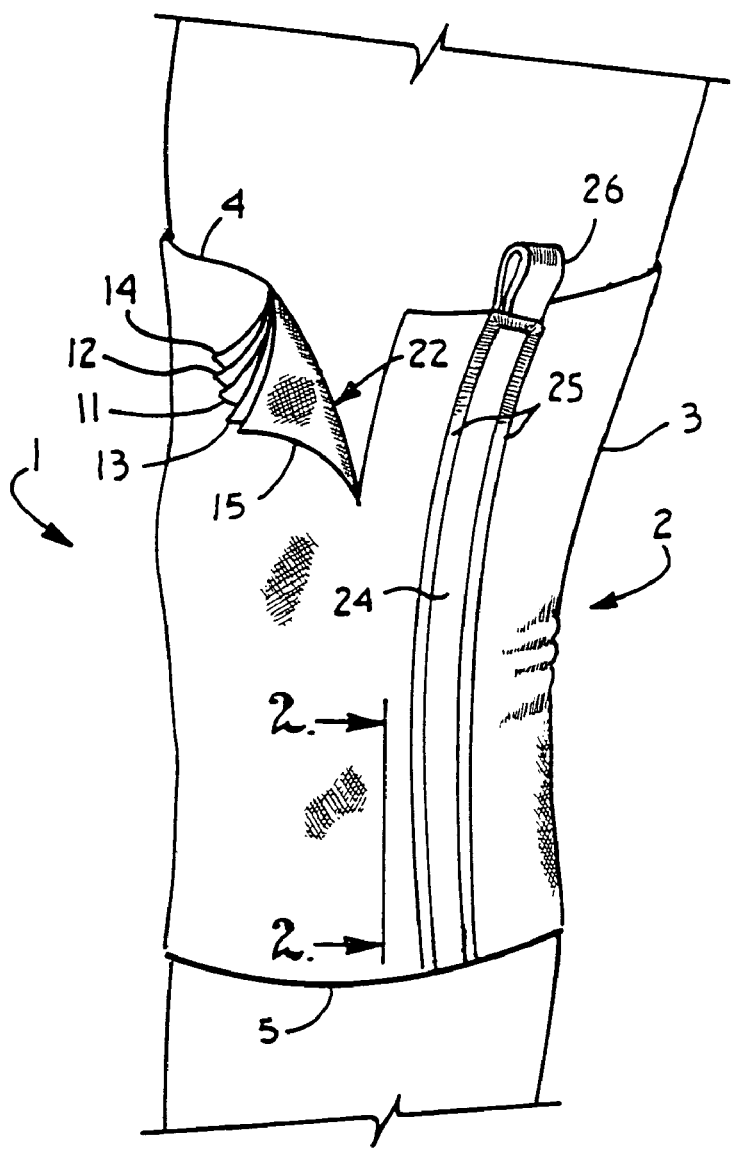
FIG. 1 is a side elevational view of a compression device in accordance with the present invention shown placed on the leg of a user, with a portion of the support cut and laid back so as to illustrate the multilayer laminate construction thereof.
Figure 2:
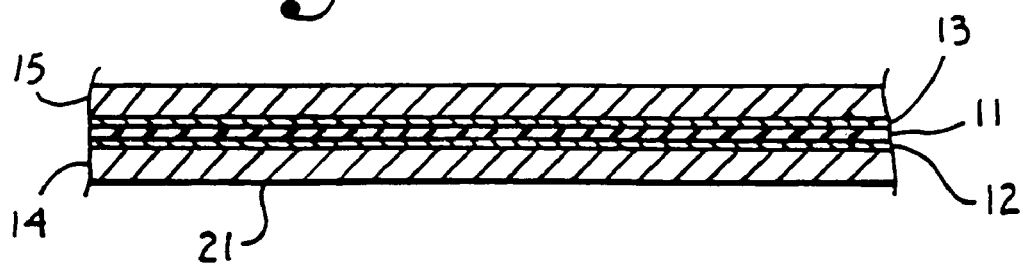
FIG. 2 is a fragmentary cross-sectional view of the compression device, taken along line 2-2 of FIG. 1.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

In accordance with the present invention, the reference numeral 1 generally indicates a compressive moisture control device. The device 1 of the present embodiment is a compression support sleeve and the sleeve 1 is depicted in place over a human leg knee joint area 2. The sleeve 1 includes a generally tube-shaped elastomeric member 3 of multilayer construction, having an upper end 4 and a lower end 5.

As best shown in FIGS. 1 and 3, a central film 11 is sandwiched between outer and inner adhesive layers 12 and 13. A flexible and resilient film composition is required for the film 11 in order to permit stretching of the sleeve 1, as it is put on and to accommodate movement of the underlying joint or limb during use. Polyurethane having a thickness of about 2 to 3 mils is preferred, although another suitable polymeric film may be employed and thickness may vary in accordance with desired characteristics of the sleeve 1.

The central film 11 is preferably constructed of a hydrophillic macroporous polyurethane foam membrane which actively attracts moisture thereto. A foam membrane of this type which is suitable for many applications is sold by Povair International Limited of Estuary Road, King's Lynn, Norfolk, PE30 2HS, England under the trademark "PORELLE®" which is supplied on a polyester carrier substrate and has a thickness of about 250 micrometers.

The adhesive or heat and pressure sensitive glue layers 12 and 13 are bonded respectively to outer and inner layers of elastomeric polymer material 14 and 15. Any suitable adhesive which is compatible with both the polyurethane film layer 11 and the elastomeric polymer layers 14 and 15 and which will not block moisture passage may be employed. Such adhesives are well known in the art. The polymer layers 14 and 15 are preferably constructed of a spandex fiber such as is sold under the trademark Lycra by DuPont Chemical Co., however, other materials function satisfactorily for the purpose.

In certain embodiments of the invention wherein it is especially desirable for moisture to be conveyed away from the skin of a user, the polymer layers 14 and 15 are preferably constructed of polyester microfibers wherein the denier is approximately 100 and the filament count per fiber is approximately 144. Where even more moisture control is required, the microfiber can have a filament gradient wherein a greater number of smaller diameter filaments are utilized to produce a fiber of a given denier on the side of the fiber closest to the skin in comparison to the opposite side of the fiber.

The outer elastomeric polymer layer 14 presents a smooth surface 21, which facilitates free movement of clothing over the sleeve 1, while providing resistance to abrasion and wear. The inner polymer layer 15 has an inner surface which is compatible with engagement with skin without being abrasive. It is foreseen that the interior polymer layer 14 may be constructed of woven or non-woven fabric The sleeve 1 may also include one or more ribs or stays 24, which are formed of a flexible synthetic resinous material to impart additional rigidity and support to the garment or assist in application of the sleeve 1 to the knee joint 2. The stays 24 are secured in place on either side and at the ends by seams 25, which may be sewn or fusion welded. One or more loops 26 extend upwardly from sleeve upper end 4 to facilitate pulling the garment on and positioning it snugly in place over a selected limb or joint.

While a generally tubular sleeve 1 has been depicted and described, those skilled in the art will appreciate that such compression support garments may be fabricated to include gussets or seams or in the form of stockings, spiral constructions for use on the ankles and elbows.

It is foreseen that compressive planar bandages may also be constructed in accordance with the invention that may be wound around a limb or joint in overlapping fashion and held in place by hook and loop fasteners or clips, used for wound care or the like. Such bandages may be constructed of elastomeric material and be flexible and elastic or opposite ends of the bandages may be designed to allow an applier to pull the opposite ends during application and secure the ends using hook and loop fasteners or the like so as to apply suitable compression when needed.

A method of manufacture of the material of sleeve 1 is depicted schematically in FIG. 4 which includes providing a substrate 32 having suitable release properties to permit casting and easy removal of a polyurethane solution. The substrate 32 is preferably supplied on a spool 33. As the substrate 32 is unrolled into an assembly line, it passes a spray station 34, which applies a polyurethane fluid 35 to one surface of the substrate 32. The polyurethane coated substrate 32 passes through a series of drying ovens 36 and 37, which dry the polyurethane 35 into a 2 mil film 38 on the substrate 32. The film 11 and substrate 32 may be manufactured by a remote process from the remainder of the process.

The film-coated substrate passes a spray station 44, which applies an adhesive solution 45 onto the surface. Preferably, the station 44 sprays adhesive solution 45 onto the film-coated substrate in an even, continuous layer. In other alternate embodiments, the spray station 44 may be operated intermittently or the distance between the spray heads may be set to deliver a discontinuous layer of adhesive solution 45. Once coated with adhesive solution 45, the polyurethane film-coated substrate 32 passes through a second series of ovens 46 and 47, where the solvent is evaporated from the adhesive solution to form an adhesive layer 48.

Elastomeric fabric 54, such as a spandex fiber of about 20 mils, is supplied, preferably on a spool 55. For the fabric 54 knitted nylon tricot fabric, especially as sold under the trademark LYCRA by E. I. DuPont de Nemours, may be utilized, although any other suitable knitted, woven or nonwoven fabric such as cotton, rayon, other stretchable synthetic fiber or blend thereof may be employed. The fabric 54 is unwound onto the surface of the adhesive layer 48 and is pressed into the adhesive 48 at elevated temperature by a series of rollers 56 and 57 to form a fabric/adhesive/film laminate 58. The laminate 58 is then stripped from the substrate 32, exposing an uncoated polyurethane film surface 59.

The laminate 58 passes a spray station 65 which again sprays an adhesive solution 66 onto the uncoated polyurethane film surface 59. Once coated with adhesive solution 66, the laminate 58 passes through a third series of drying ovens 67 and 68, where the solvent is evaporated from the adhesive solution to form an adhesive layer 69.

Additional elastomeric tricot fabric 75 of about 20 mils in thickness is supplied on a spool 76. The fabric 75 is unwound onto the surface of the adhesive layer 69 and is pressed into the adhesive 69 by rollers 77 and 78 to form a fabric/adhesive/polyurethane/adhesive/fabric laminate material 79.

The laminate 79 passes through a series of circulating air ovens 98, 99 for evaporation of any solvent residue and curing. The laminate 79 is then wound onto rolls 100 of manageable size.

The material thus produced may be formed into completed sleeves 1, stockings and other types of compression support having sewn or fused darts, gussets, and seams. The supports may also include fasteners such as for example, hooks, zippers, buttons and the like.

It is to be understood that while certain forms of the present invention have been illustrated and described herein, it is not to be limited to the specific forms or arrangement of parts described and shown.

What is claimed and desired to be secured by Letters Patent is as follows:

1. A breathable and compressive moisture management device for use with a patient comprising:
    a) a first layer of a fiber material adapted to engage the skin of a user;
    b) a second layer of a hydrophillic polyurethane foam; said foam presenting a pair of opposed surfaces;
    c) a third layer of a fiber material;
    d) a pair of adhesive layers bonding said first and third layers to respective second layer surfaces; and wherein
    e) said first layer is an inner layer and is a microfiber having a larger ratio of filaments per fiber positioned to contact a user during use as compared to filaments per fiber opposite the user so as to draw moisture toward said hydrophillic foam.
2. The device according to claim 1 wherein:
    a) said device is a flexible elastomeric sleeve.
3. The device according to claim 1 wherein:
    a) said third layer has a larger ratio of filaments per fiber near said foam than filaments per fiber located on an exterior surface thereof.
4. The device according to claim 1 for supporting a joint or limb of the body, wherein:
    a) said device is sized and shaped so as to form a limb encircling sleeve.
5. The device according to claim 4 wherein:
    a) said compression support device further includes a support rib.
6. A method for making a stretchable multilayer laminate material for use in orthopedic moisture management devices for the body, comprising:
    a) providing a film of a substrate material and applying a surface of the substrate with a coating of a hydrophillic polyurethane foam;
    b) spraying a first and exposed surface of said foam with a coating of an adhesive composition;
    c) providing a first layer of a fiber material and bonding the material to the adhesive coating to form a laminate;
    d) removing the substrate film from the laminate to expose a second polymer film surface;
    e) spraying the second polymer film surface with a coating of an adhesive composition; and
    f) providing a second layer of a fiber material and bonding the second layer of fiber material to the adhesive coating.
7. The method according to claim 5 wherein said fiber material comprises an elastomeric fiber.
8. A breathable and moisture managing material for use in the production of orthopedic devices; said material comprising:
    a) a first fabric layer having a first side adapted to engage skin of a user and a second side;
    b) a first adhesive layer applied to said first fabric second side;
    c) a hydrophillic polyurethane macroporous foam having a first side adhered to said first adhesive layer and a second side;
    d) a second adhesive layer bound to said foam second side;
    e) a second fabric layer having a first side adhered to said second adhesive layer and a second side that is adapted to be exposed to ambient air during use of said material; and wherein
    f) said first fabric is constructed of a microfiber having comparatively more filaments per fiber on the first side thereof and fewer filaments on the second side thereof.
9. The material according to claim 8 wherein:
    a) said second fabric is constructed of a microfiber having comparatively more filaments per fiber on the first side thereof and fewer filaments per fiber on the second side thereof such that during use, moisture is urged from skin engaged by said material to said second fabric second side for evaporation into ambient air.
10. A flexible and breathable orthopedic moisture management device comprising:
    a) a first layer of a moisture wicking, flexible and absorbent fiber material adapted to engage the skin of a user;
    b) a second layer of a hydrophillic polyurethane foam; said foam presenting a pair of opposed surfaces; said first layer adapted to draw moisture from the skin of a user and transfer the moisture to the polyurethane foam;
    c) a third layer of an absorbent and flexible fiber material;
    d) a pair of adhesive layers bonding said first and third layers to respective second layer surfaces; and
    e) each of said layers assembled in a supporting orthopedic sleeve.
11. The device according to claim 10 wherein:
    a) said sleeve is elastomeric and provides compression to a user.
12. A method of controlling moisture on the skin of a person the steps of:
    a) providing a material having a first and a second layer of flexible and absorbent fiber with a layer of hydrophillic polyurethane foam therebetween wherein the first layer is adapted to draw moisture from the skin of a user and transfer the moisture to the hydrophillic polyurethane; and
    b) applying said material to the skin under compression such that said first layer of fiber at least partially engages the skin and draws moisture from the skin to the hydrophillic polyurethane.
13. The method according to claim 12 including the step of:
    a) constructing said fiber layers out of a polyester microfiber.
14. A breathable and compressive moisture management device for use with a patient comprising:

a) a first layer of a fiber material adapted to engage the skin of a user; said first layer being an inner layer and being a microfiber having a larger ratio of filaments per fiber positioned to contact a user during use as compared to filaments per fiber opposite the user so as to draw moisture from a user's skin;

b) a second layer of a hydrophillic polyurethane foam; said foam presenting a pair of opposed surfaces; the first layer of fabric drawing moisture to the polyurethane foam;

c) a third layer of a fiber material; and d) a pair of adhesive layers bonding said first and third layers to respective second layer surfaces.

15. A breathable and compressive moisture management device for use with a patient comprising:

a) a first layer of a fiber material adapted to engage the skin of a user;

b) a second layer of a hydrophillic polyurethane foam adhered to said first layer; said first layer of fiber adapted to draw moisture from the skin of a user to the polyurethane foam; said foam presenting a pair of opposed surfaces;

c) a third layer of a fiber material adhered to said second layer; said third layer adapted to draw moisture from the polyurethane foam such that when said device is placed in contact with a user, the device draws water in a liquid form from the skin of a user to an exterior of the third layer.

* * * * *